(12) United States Patent
Takama

(10) Patent No.: US 9,442,122 B2
(45) Date of Patent: Sep. 13, 2016

(54) METHOD FOR ASSAYING BILIRUBIN AND ASSAY INSTRUMENT USED IN BILIRUBIN ASSAY

(75) Inventor: Toshio Takama, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 1222 days.

(21) Appl. No.: 12/526,214

(22) PCT Filed: Apr. 17, 2008

(86) PCT No.: PCT/JP2008/057475
§ 371 (c)(1),
(2), (4) Date: Aug. 6, 2009

(87) PCT Pub. No.: WO2008/136273
PCT Pub. Date: Nov. 13, 2008

(65) Prior Publication Data
US 2010/0323382 A1      Dec. 23, 2010

(30) Foreign Application Priority Data
Apr. 27, 2007   (JP) .................................. 2007-119480

(51) Int. Cl.
*C12Q 1/26*   (2006.01)
*G01N 33/72*   (2006.01)
*G01N 21/78*   (2006.01)
(Continued)

(52) U.S. Cl.
CPC ............... *G01N 33/728* (2013.01); *C12Q 1/26* (2013.01); *G01N 21/78* (2013.01); *G01N 33/523* (2013.01); *G01N 2021/0325* (2013.01); *G01N 2021/7773* (2013.01); *G01N 2021/7783* (2013.01); *G01N 2800/085* (2013.01)

(58) Field of Classification Search
CPC .................................................. G01N 33/728
See application file for complete search history.

(56) References Cited

U.S. PATENT DOCUMENTS 4,554,249 A * 11/1985 Kosaka et al. .................. 435/10
4,571,383 A *  2/1986 Takayama et al. ............. 435/25
(Continued)

FOREIGN PATENT DOCUMENTS

EP     0 005 637     11/1979
EP     1 557 660      7/2005
(Continued)

OTHER PUBLICATIONS

Doumas, et al., "Determination of the Sum of Bilirubin Sugar Conjugates in Plasma by Bilirubin Oxidase", Clinical Chemistry 45:8, pp. 1255-1260, 1999.
(Continued)

*Primary Examiner* — Taeyoon Kim
*Assistant Examiner* — Tiffany Gough
(74) *Attorney, Agent, or Firm* — Morgan, Lewis & Bockius LLP

(57) ABSTRACT

A method for assaying bilirubin in which a dry reagent is used, which is capable of accelerating the reaction of bilirubin oxidase, and an assay instrument to be used in the method for assaying bilirubin, are provided. The method for assaying bilirubin is characterized in that a biological sample and a bilirubin oxidase-containing dry reagent are mixed first, and then the mixture obtained and a surfactant-containing dry reagent are mixed. An assay instrument (1) to be used in bilirubin assay is characterized in that a bilirubin oxidase and a surfactant are arranged in any of a sample supply part (11), passages (12, 13, 14), and a detection part (15) in a manner such that the bilirubin oxidase is positioned closer to the sample supply part (11) than the surfactant is.

11 Claims, 6 Drawing Sheets

(51) Int. Cl.
*G01N 33/52* (2006.01)
*G01N 21/03* (2006.01)
*G01N 21/77* (2006.01)

(56) References Cited

U.S. PATENT DOCUMENTS

| | | | |
|---|---|---|---|
| 4,985,360 A * | 1/1991 | Takahashi et al. | 435/25 |
| 5,104,794 A | 4/1992 | Kondo et al. | |
| 2006/0046206 A1 | 3/2006 | Meagley et al. | |
| 2008/0169206 A1 * | 7/2008 | Pei et al. | 205/780.5 |

FOREIGN PATENT DOCUMENTS

| | | |
|---|---|---|
| JP | 59-130198 | 7/1984 |
| JP | 62-105047 | 5/1987 |
| JP | 62-282598 | 12/1987 |
| JP | 63-52060 | 3/1988 |
| JP | 63-52064 | 3/1988 |
| JP | 2-238897 | 9/1990 |
| JP | 11-123099 | 5/1999 |
| JP | 2004-150803 | 5/2004 |
| JP | 2006-34178 | 2/2006 |
| WO | 86/00933 | 2/1986 |

OTHER PUBLICATIONS

Grohmann, et al., "Bilirubin Measurement for Neonates: Comparison of 9 Frequently Used Methods", Pediatrics, vol. 117, No. 4, pp. 1174-1183, Apr. 2006.

Office Action issued in Japanese Application No. 2008-531474 mailed Mar. 10, 2011.

* cited by examiner

METHOD FOR ASSAYING BILIRUBIN AND ASSAY INSTRUMENT USED IN BILIRUBIN ASSAY

TECHNICAL FIELD

The present invention relates to a method for assaying bilirubin and an assay instrument used in the bilirubin assay.

BACKGROUND ART

Bilirubin is a dye that is present mostly in bile in a living body, and mainly is produced from hemoglobin when senescent red blood cells, whose principal component is hemoglobin, are decomposed and metabolized in the marrow, the thymus, the liver, and the like. Bilirubin produced from hemoglobin is bound with albumin in blood, and is called unconjugated (indirect) bilirubin. This unconjugated bilirubin is taken into the liver and conjugated with glucuronic acid, thereby becoming conjugated (direct) bilirubin, and is discharged to the bile duct. Unconjugated (indirect) bilirubin and conjugated (direct) bilirubin collectively are called total bilirubin. Generally most of total bilirubin is indirect bilirubin.

The clinical significance in the assay of bilirubin in a biological sample has been well known conventionally. For example, hepatocellular disorder, intrahepatic cholestasis, extrahepatic cholestasis, or the like can be predicted from an increase in a direct bilirubin amount, while an increase in the amount of produced bilirubin, liver function abnormality, or the like can be predicted from an increase in an indirect bilirubin amount. As described above, the total bilirubin amount is an amount of a sum of the direct bilirubin amount and the indirect bilirubin amount. Therefore, if the total bilirubin amount and the direct bilirubin amount are known, the indirect bilirubin amount can be determined.

As methods for assay of bilirubin, the diazo method, the vanadate method, the enzyme method, the high precision liquid chromatography (HPLC) method, and the like are known. The enzyme method is a method in which an enzyme such as a bilirubin oxidase is allowed to act on a bilirubin-containing sample so as to oxidize bilirubin into biliverdin, whereby the light absorption by bilirubin (maximum absorption wavelength: 450 nm and the vicinity of the same) is eliminated, and a concentration of bilirubin is determined based on a decrease in the absorbance.

In the case where the total bilirubin is assayed by the enzyme method, there are problems in that the reaction with a bilirubin oxidase takes time or the reaction is insufficient, owing to the binding of indirect bilirubin with albumin. To cope with these problems, a surfactant or another substance is added as a reaction accelerator, which has been disclosed (see Patent Documents 1 to 3).

Patent Document 1 discloses a liquid-system method for assaying bilirubin in which first of all a sample containing bilirubin is mixed with a buffer solution containing sodium cholate, sodium dodecyl sulfate (SDS), or the like as an agent for transforming bilirubin into a direct type, and thereafter an enzyme reagent containing a bilirubin oxidase is added to the mixture. Patent Document 2 discloses a liquid-system method for assaying bilirubin in which a sample containing bilirubin is added to a bilirubin oxidase solution containing sodium cholate, SDS, or the like as a reaction accelerator. Patent Document 3 discloses a liquid-system method for assaying bilirubin in which a bilirubin oxidase and a sample containing and bilirubin are allowed to react with each other in the presence of hydroxypyridine derivative or mercaptopyridine derivative for accelerating reaction.

Patent Document 1: JP 59 (1984)-130198 A
Patent Document 2: JP 62 (1987)-282598 A
Patent Document 3: JP 2006-34178 A

DISCLOSURE OF INVENTION

Problem to be Solved by the Invention

It is an object of the present invention to provide a method for assaying bilirubin, and an assay instrument used in a bilirubin assay, which are capable of accelerating the reaction of a bilirubin oxidase in a bilirubin assay in which a dry reagent is used.

Means for Solving Problem

In order to achieve the above-described object, the method for assaying bilirubin according to the present invention includes mixing the biological sample, a bilirubin oxidase-containing dry reagent, and a surfactant-containing dry reagent; and optically measuring a change caused by the mixing, wherein the mixing of the biological sample and the bilirubin oxidase-containing dry reagent is carried out before the mixing with the surfactant-containing dry reagent.

Further, in order to the above-described object, the assay instrument used in bilirubin assay according to the present invention includes a sample supply part for supplying a biological sample, a detection part, and a passage connected with the sample supply part and the detection part, wherein a bilirubin oxidase and a surfactant are arranged at any of the sample supply part, the passage, and the detection part in a manner such that the bilirubin oxidase is positioned closer to the sample supply part than the surfactant is.

Effects of The Invention

The inventors of the present invention made earnest studies about a method for assaying bilirubin using an enzyme (bilirubin oxidase), and took notice that in a bilirubin assay using a dry reagent, in some cases a reaction between indirect bilirubin and a bilirubin oxidase took time, and when the concentration of indirect bilirubin was high, the reaction did not end within a predetermined period. Then, they found that by mixing a dry-reagent-type surfactant after mixing a bilirubin oxidase in a dry reagent with a sample to be subjected to assay (hereinafter such a sample is referred to as "assay sample"), the efficiency of the reaction between indirect bilirubin and the bilirubin oxidase can be improved, whereby the bilirubin assay can be carried out within a short period. As a result, they arrived at the present invention. It should be noted that conventionally in a liquid-system method for assaying bilirubin, it was usual that a bilirubin oxidase reaction accelerator such as a surfactant was mixed with a sample before or at the same time when a bilirubin oxidase was mixed with the sample, as described above (see Patent Documents 1 to 3 shown above).

According to the present invention, for example, the reaction between bilirubin in an assay sample and a bilirubin oxidase can be allowed to occur efficiently and sufficiently. Therefore, preferably, the time needed for the bilirubin assay can be shortened, and/or the accuracy and the reproducibility of the bilirubin assay can be improved.

Figure 1A:
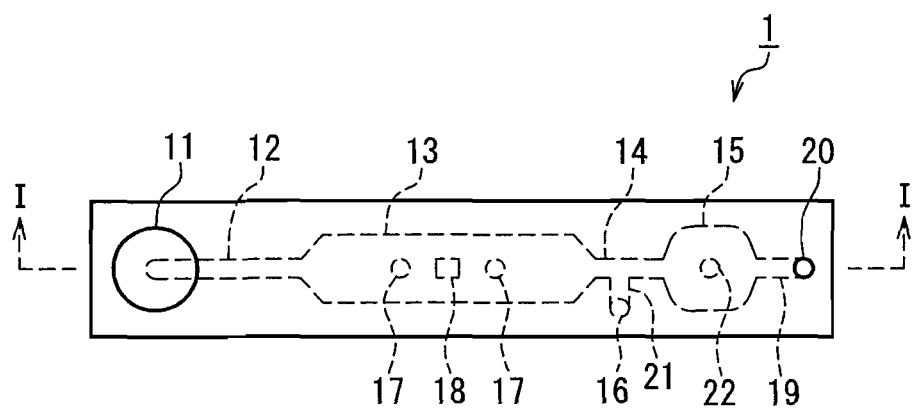
FIG. 1A is a plan view showing an exemplary assay instrument of the present invention.

DESCRIPTION OF REFERENCE NUMERALS 1, 2 . . . assay instrument
11 . . . sample supply part
12 . . . sample supply passage
13 . . . first reagent arrangement part
14 . . . connection passage for connecting reagent arrangement parts
15 . . . detection part/second reagent arrangement part
16 . . . air vent for first reagent arrangement part
17 . . . bilirubin oxidase-containing dry reagent
18 . . . magnetic particle
19 . . . air vent passage for second reagent arrangement part
20 . . . air vent for second reagent arrangement part
21 . . . air vent passage for first reagent arrangement part
22 . . . surfactant-containing dry reagent
111 . . . substrate
112 . . . cover

DESCRIPTION OF THE INVENTION

As described above, the present invention is based on the findings that in a dry-system method for assaying bilirubin in which at least a bilirubin oxidase-containing dry reagent and a surfactant-containing dry reagent are used, the efficiency of reaction of bilirubin, or preferably indirect bilirubin, with a bilirubin oxidase can be improved and the assay time can be shortened by setting the order of contact of an assay sample with the foregoing two dry reagents so that the contact with the bilirubin oxidase-containing dry reagent precedes the contact with the surfactant-containing dry reagent. Details are not clear regarding the mechanism in which the time of reaction between indirect bilirubin and enzyme can be shortened by bringing a sample into contact with the enzyme before bringing the sample into contact with the surfactant, but it can be considered that if an assay sample is brought into contact with a surfactant-containing dry reagent, the surfactant is bound with a bilirubin-albumin complex that is indirect bilirubin, thereby hindering the reaction between bilirubin and an enzyme. In contrast, by bringing an assay sample into contact with a bilirubin oxidase-containing dry reagent first, an enzyme is bound with a bilirubin-albumin complex, and thereafter, a surfactant added thereto causes bilirubin and albumin to dissociate from each other, whereby bilirubin becomes more reactive with the enzyme. The present invention however is not limited to these mechanisms.

In the method for assaying bilirubin according to the present invention, the surfactant preferably is an anionic surfactant. Further, the anionic surfactant preferably is one or more surfactants selected from the group consisting of sodium dodecyl sulfate (SDS), sodium dodecyl benzene sulfate (SDBS), sodium polyoxyethylene lauryl ether sulfate, sodium deoxycholate, and sodium cholate.

The assay instrument of the present invention preferably is configured so that two or more of the passages connected with the same sample supply part, the passages are provided with the detection parts, respectively, and the bilirubin oxidase and the surfactant are arranged in at least one of the passages provided with the detection parts, at any of the passage and the detection part of the same, in a manner such that the bilirubin oxidase is positioned closer to the sample supply part than the surfactant is.

In the assay instrument of the present invention, the surfactant preferably is an anionic surfactant. Further, the anionic surfactant preferably is one or more surfactants selected from the group consisting of sodium dodecyl sulfate (SDS), sodium dodecyl benzene sulfate (SDBS), sodium polyoxyethylene lauryl ether sulfate, sodium deoxycholate, and sodium cholate.

In another aspect, the present invention is a test piece to be used in bilirubin assay, which is a test piece for bilirubin assay including a bilirubin oxidase-containing layer and a surfactant-containing layer, which are laminated in the stated order on a sample supply surface.

Herein in the specification of the present application, a simple recitation of "bilirubin" could refer to total bilirubin, direct bilirubin, and indirect bilirubin. Here, "direct bilirubin" refers to conjugated bilirubin, which is bilirubin conjugated with glucuronic acid, and "indirect bilirubin" refers to unconjugated bilirubin, which is bilirubin not conjugated with glucuronic acid. Direct bilirubin and indirect bilirubin collectively are referred to as total bilirubin.

In the present invention, the "bilirubin oxidase" is not limited particularly, and an enzyme capable of oxidizing bilirubin into biliverdin can be used as the bilirubin oxidase. An enzyme that is active on both direct bilirubin and indirect bilirubin is preferred as a bilirubin oxidase. An origin of a bilirubin oxidase is not limited particularly, and examples of the same include the genus *Myrothecium*, the genus *Trachyderma*, and the like, which are microorganisms. As the bilirubin oxidase, a commercially available bilirubin oxidase may be used; for example, Bilirubin Oxidase "Amano" 3 (trade name) produced by Amano Enzyme Inc., Bilirubin Oxidase "Takara" (trade name) produced by Takara Shuzo Co., Ltd., and the like can be used. In the present invention, the enzyme unit (U) for a bilirubin oxidase is indicative of a value indicated by a manufacturer if it is a commercially available bilirubin oxidase, or is indicative of an enzyme amount of a bilirubin oxidase that is capable of oxidizing 1 µmol of a substrate (albumin-bound bilirubin) under conditions of 37° C. and pH 7.0 in one minute.

In the present invention, the "surfactant" may be a conventionally known surfactant, examples of which may include anionic surfactants, nonionic surfactants, amphoteric surfactants, and cationic surfactants. One of these surfactants may be used alone, or a plurality of the same may be used in combination.

As the anionic surfactant, a conventionally known anionic surfactant may be used, examples of which include sodium alkyl sulfates such as sodium dodecyl sulfate (SDS); sodium linear alkylbenzene sulfonates such as sodium dodecyl benzene sulfonate (SDBS); sodium alkyl ether sulfates such as sodium polyoxyethylene lauryl ether sulfate; sodium deoxycholate; and sodium cholate. As the anionic surfactant used in the present invention, SDS or sodium cholate is preferred, and it also is preferable to use SDS and sodium cholate in combination. As the nonionic surfactant, a conventionally known nonionic surfactant can be used, examples of which include polyoxyethylene alkyl ether, polyoxyalkylene alkyl ether, polyoxyalkylene carboxylic acid ester, polyoxyalkylene carboxylic acid diester, polyoxyethylene polyoxypropylene copolymer (e.g. "Pluronic" (registered trademark, BASF AG) F-88), polyoxyethylene polyoxyalkylene copolymer, sucrose aliphatic acid ester, sorbitan aliphatic acid ester, and polyoxyethylene alkyl phenyl ether. As the amphoteric surfactant, a conventionally known amphoteric surfactant can be used, examples of which include sodium alkylamino fatty acid, alkyl betaine, and alkylamine oxide. As the cationic surfactant, a conventionally known cationic surfactant can be used, examples of which include alkyl trimethyl ammonium salts such as cetyl trimethyl ammonium bromide; and alkyl pyridinium salts such as cetyl pyridinium chloride and lauryl pyridinium chloride.

In the present invention, the "biological sample" refers to a sample that originates from a biological body containing bilirubin. It preferably is in a liquid form, and more preferably contains indirect bilirubin. Such a biological sample is not limited particularly, and examples of the same include bodily fluids such as whole blood, blood serum, blood plasma, and urine. The biological sample in the present invention may be diluted or treated preliminarily as required.

The method for assaying bilirubin according to the present invention may be applied to a sample other than the above-mentioned "biological sample", as a matter of course. For example, the method may be applied to a standard sample of bilirubin. Therefore, the method for assaying bilirubin according to the present invention, in another aspect, includes bringing an assay sample into contact with a bilirubin oxidase-containing dry reagent and a surfactant-containing dry reagent, and optically measuring a change occurring therefrom, whereby the contact of the assay sample with the bilirubin oxidase-containing dry reagent is carried out prior to the contact of the assay sample with the surfactant-containing dry reagent. In the present invention of this aspect, the assay sample may contain the above-described "biological sample", preferably is in a liquid form, and further preferably contains indirect bilirubin.

Next, the method for assaying bilirubin according to the present invention will be described below.

First, a bilirubin oxidase-containing dry reagent and a surfactant-containing dry reagent are prepared. In the method for assaying bilirubin according to the present invention, the "bilirubin oxidase-containing dry reagent" refers to a reagent obtained by subjecting a bilirubin oxidase-containing reagent solution to a drying treatment. The drying treatment is not limited particularly as long as it is a method that would not damage the enzymatic activity of the bilirubin oxidase, and it may be a conventional drying treatment such as freeze-drying, heat-drying, air-drying, or vacuum-drying. From the viewpoint of maintaining the enzymatic activity, freeze-drying is preferred. A reagent solution containing a bilirubin oxidase, before being dried, may contain a buffer, a pH regulator, a stabilizer, a chelating agent, and the like in addition to the bilirubin oxidase. It is preferable that a surfactant should not be contained in the bilirubin oxidase-containing dry reagent. As will be described later, separately from this, a surfactant in a surfactant-containing dry reagent is to be mixed with the biological sample.

As a buffer contained in the bilirubin oxidase-containing reagent solution before being dried, a conventionally known buffer that exhibits a buffering ability at a pH in a range of 6.0 to 8.0can be used, for example. Examples of the foregoing buffer include a phosphoric acid buffer, a tris buffer, a boric acid buffer, Good's buffer, a TES(N-tris (hydroxymethyl)methyl-2-aminoethanesulfonic acid), BES (N,N-bis(2-hydroxyethyl)-2-aminoethanesulfonic acid), MOPSO (2-hydroxy-3-morpholinopropanesulfonic acid), MOPS (3-(N-morpholino)propanesulfonic acid), PIPES (piperazine-N,N'-bis(2-ethane sulfonic acid)), ADA (N-(2-acetamide) iminodiacetic acid), ACES (N-(2-acetamide)-2-aminoethanesulfonic acid), and MES (2-morpholinoethanesulfonic acid). Among these, BES, MOPSO, MOPS, and ACES are preferred. The bilirubin oxidase-containing reagent solution before being dried may be treated so that pH thereof is adjusted as required. The pH of the reagent solution is, for example, in a range of 5.5 to 8.0, and preferably in a range of 6.0 to 7.5.

The bilirubin oxidase-containing dry reagent preferably contains bilirubin oxidase in an amount sufficient for reaction with bilirubin in a biological sample when it is dissolved in the biological sample. The content of the enzyme can be set easily by any person skilled in the art. For example, in the case where the biological sample is blood, a final concentration of bilirubin oxidase after being dissolved in the biological sample is, for example, 1 to 100 U/ml, and preferably 3 to 10 U/ml. In the case where the bilirubin oxidase-containing dry reagent contains a buffer, the buffer preferably is in a concentration such as to exhibit a buffering ability sufficient for maintaining the activity of bilirubin oxidase when the reagent is dissolved in a biological sample.

In the method for assaying bilirubin according to the present invention, the "surfactant-containing dry reagent" refers to a reagent obtained by subjecting a surfactant-containing reagent solution to a drying treatment. The drying treatment is not limited particularly, and examples of the same include a conventional drying treatment such as freeze-drying, heat-drying, air-drying, or vacuum-drying. The kinds of the surfactant contained in the reagent solution are as described above. The reagent solution may contain a bilirubin oxidase, a buffer, a pH regulator, a stabilizer, and the like as required. As the buffer, the same as those that can be contained in the bilirubin oxidase-containing dry reagent can be used.

The surfactant-containing dry reagent preferably contains a surfactant in an amount sufficient for accelerating the reaction of a bilirubin oxidase when the reagent is dissolved in a biological sample. A final concentration of a surfactant after being dissolved in a biological sample is, for example, 0.3 to 2 percent by mass (mass %), preferably 0.5 to 2 mass %, and more preferably 1.0 to 1.5 mass %. As described above, in the surfactant-containing dry reagent, two or more kinds of surfactants may be contained in amounts with which the above-described final concentration is to be achieved.

Next, the mixing of the biological sample with the bilirubin oxidase-containing dry reagent (first mixing) is carried out, and subsequently the mixing of the product obtained as a result of the first mixing with the surfactant-containing dry reagent (second mixing) is carried out. The method for mixing is not limited particularly, and the mixing may be carried out by, for example, using a magnetic stirring bar or a magnetic particle and applying an appropriate magnetic field from the outside. The first mixing can be completed when the bilirubin oxidase-containing dry reagent is dissolved. The second mixing may be carried out continuously after the completion of the first mixing, or may be carried out with an interval provided after the first mixing. From the viewpoint of shortening the time for bilirubin assay, the interval between the first mixing and the second mixing preferably is short.

In the method for assaying bilirubin according to the present invention, the "change caused by" the first and second mixings refers to a change such that bilirubin is oxidized into biliverdin. The "optically measuring" of the foregoing change refers to the optically observing of disappearance of bilirubin that exhibits maximum absorption in the vicinity of 450 nm. For example, the foregoing measurement includes the measurement of an absorbance of a biological sample at 450 nm before the first mixing and the measurement of an absorbance at 450 nm after the second mixing. The concentration of bilirubin can be determined from the difference between the foregoing absorbances. The optical measurement method in the method for assaying bilirubin according to the present invention is, for example, the absorbance measurement utilizing transmitted light, though not being limited thereto; a method utilizing reflected light or scattered light, for example, may be used.

Next, an assay instrument of the present invention is described below.

An assay instrument according to the present invention is an assay instrument used in the method for assaying bilirubin, and includes a sample supply part for supplying the foregoing biological sample; a detection part; and a passage connected with the sample supply part and the detection part, wherein a bilirubin oxidase and a surfactant are arranged at any of the sample supply part, the passage, and the detection part in a manner such that the bilirubin oxidase is positioned closer to the sample supply part than the surfactant is. The structure and form of the assay instrument of the present invention is not limited particularly, as long as the bilirubin oxidase and the surfactant are arranged in a manner such that the bilirubin oxidase is positioned closer to the sample supply part than the surfactant is. The assay instrument according to the present invention preferably is used in the method for assaying bilirubin according to the present invention.

The passage preferably is a passage capable of causing the biological sample to travel utilizing the capillary phenomenon. The bilirubin oxidase and the surfactant arranged therein preferably are in the forms of the above-described bilirubin oxidase-containing dry reagent and the surfactant-containing dry reagent, respectively.

In the foregoing passage, a reagent arrangement part may be formed as required. In the case where two reagent arrangement parts are formed, a bilirubin oxidase and a surfactant can be arranged therein, respectively. Alternatively, the configuration may be such that one reagent arrangement part is formed and a bilirubin oxidase is arranged therein, while a surfactant is arranged in the detection part. The method of arranging the reagents, though not being limited, may be such that the bilirubin oxidase-containing reagent solution and the surfactant-containing reagent solution are prepared as described above, applied by the ink-jet method or the like, and dried. As the drying treatment, a conventional drying treatment such as freeze-drying, heat-drying, air-drying, or vacuum-drying can be used. In the case of an enzyme, freeze-drying is preferred. To aid the mixing of the same with a biological sample, a magnetic stirring bar or a magnetic particle may be arranged in the reagent arrangement part.

An embodiment of the assay instrument according to the present invention is described below, with reference to FIGS. 1A and 1B. FIG. 1A is a plan view of an assay instrument 1 of the present invention, and FIG. 1B is a cross-sectional view of the same taken along a line I-I in FIG. 1A, as viewed in a direction indicated by the arrows.

As shown in the drawings, the assay instrument 1 has a configuration in which a cover 112 is provided on a substrate 111. Inside the substrate 111, a first reagent arrangement part 13 and a second reagent arrangement part 15 that functions as a detection part, too (hereinafter this part is referred to also as "the detection part/second reagent arrangement part), are formed, and the two parts are connected with each other via a connection passage 14 for connecting the reagent arrangement parts. In the cover 112, an aperture is formed, which is a sample supply part 11. The sample supply part 11 and the first reagent arrangement part 13 are connected with each other via a sample supply passage 12. The first reagent arrangement part 13 is connected with an air vent 16 for the first reagent arrangement part, via an air vent passage 21 for the first reagent arrangement part, which branches from the connection passage 14 for connecting the reagent arrangement parts. The detection part/second reagent arrangement part 15 is connected with an air vent 20 for the second reagent arrangement part, via an air vent passage 19 for the second reagent arrangement part. The air vent 16 for the first reagent arrangement part and the air vent 20 for the second reagent arrangement part are closed before use. In the first reagent arrangement part 13, a bilirubin oxidase-containing dry reagent 17 and one magnetic particle 18 are arranged. In the detection part/second reagent arrangement part 15, a surfactant-containing dry reagent 22 is arranged. It should be noted that a magnetic particle may be arranged in the detection part/second reagent arrangement part 15.

In the present invention, materials of members constituting the assay instrument are not limited particularly. A material for the substrate and the cover may be, for example, polystyrene, polymethyl methacrylate, polydimethyl siloxane, polyethylene terephthalate, glass, or the like. For example, a translucent material preferably is used for the detection part 15 so that optical measurement, for example, spectroscopic measurement by measuring transmitted light, can be performed. The size of the assay instrument of the present invention is not limited particularly, and may be set appropriately by any person skilled in the art. Further, the method for manufacturing the assay instrument of the present invention is not limited particularly, either, and it may be manufactured by a conventionally known method.

Figure 1B:
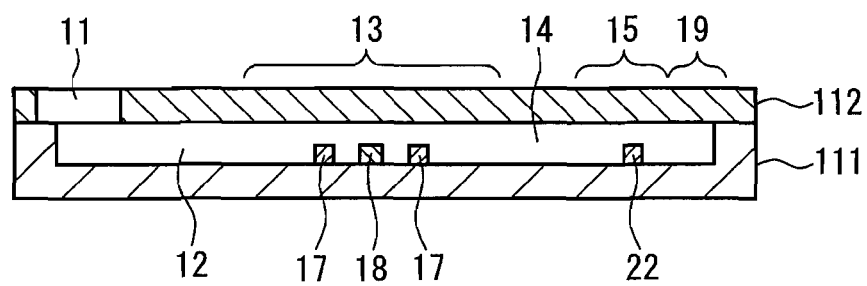
FIG. 1B is a cross-sectional view of the same taken along a line I-I in FIG. 1A, as viewed in a direction indicated by the arrows.

A method for assaying bilirubin using the assay instrument shown in FIGS. 1A and 1B is performed, for example, as described below. First, a biological sample is supplied to the sample supply part 11. Then, the air vent 16 for the first reagent arrangement part is opened. The opening of the air vent 16 causes the capillary phenomenon, which allows the sample to be introduced into the first reagent arrangement part 13 via the sample supply passage 12, thereby to dissolve the bilirubin oxidase-containing dry reagent 17. Then, the magnetic particle 18 is moved by a magnetic body (not shown) so as to agitate the biological sample, thereby mixing and dissolving the dry reagent uniformly. Next, the air vent 20 for the second reagent arrangement part is opened, to cause the capillary phenomenon, which allows the biological sample to be introduced into the detection part/second reagent arrangement part 15 via the connection passage 14 for connecting the reagent arrangement parts. Here, the biological sample in the state of containing the magnetic particle 18 may be introduced. Then, in the detection part/second reagent arrangement part 15, the biological sample may be agitated by the magnetic particle 18 as required, whereby the surfactant-containing dry reagent 22 is mixed and dissolved uniformly, and the reaction of the bilirubin oxidase is accelerated. Here, the magnetic particle 18 preferably is removed out of the detection part/second reagent arrangement part 15 as required. Then, in the detection part/second reagent arrangement part 15, an absorbance (450 nm) after the reaction and the like is measured by an optical scheme (e.g. by using a spectro-photometer).

The assay instrument according to the present invention, in another aspect, includes two or more of the passages connected with the same sample supply part, the passages are provided with the detection parts, respectively, and the bilirubin oxidase and the surfactant are arranged in at least one of the passages provided with the detection parts, at any of the passage and the detection part of the same, in a manner such that the bilirubin oxidase is positioned closer to the sample supply part than the surfactant is (hereinafter this assay instrument is referred to also as assay instrument assembly). With this configuration, one biological sample flows into a plurality of passages and reacts with various reagents; this makes it possible to subject one biological sample to measurements of various items other than bilirubin, too. It should be noted that in the assay instrument assembly of the present invention having two or more passages, it is preferable that in at least one set of the passage and the detection part, the bilirubin oxidase is not arranged, so that the set of the passage and the detection part provides a control concerning the bilirubin assay. This configuration makes it possible to eliminate the need for measurement of an absorbance of a biological sample before reaction with use of an assay instrument separately, and allows the bilirubin assay to be performed with use of only one assay instrument assembly of the present invention alone. Further, the assay instrument assembly of the present invention may be in a form as shown in FIG. 2.

Figure 2:
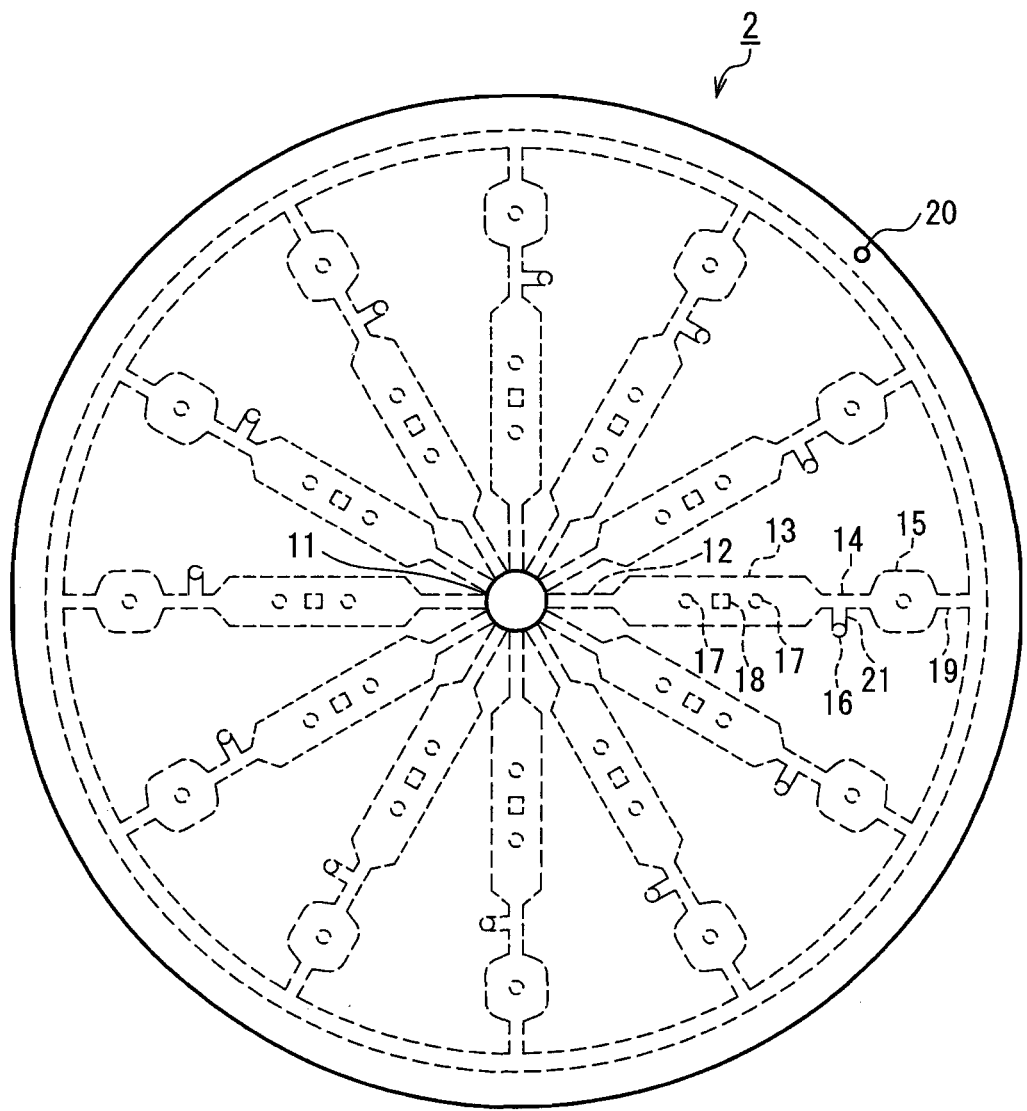
FIG. 2 is a plan view of another exemplary assay instrument of the present invention.

The assay instrument assembly shown in FIG. 2 is an assay instrument assembly in a form such that the assay instruments, each of which has one passage as shown in FIGS. 1A and 1B, are assembled in a radial form. In FIG. 2, members similar to those in FIGS. 1A and 1B are designated with the same reference numerals. As shown in the drawing, the assay instrument assembly 2 is composed of twelve assay instruments each of which is formed as shown in FIGS. 1A and 1B. Each assay instrument includes a sample supply part 11, a sample supply passage 12, a first reagent arrangement part 13, an air vent passage 21 for the first reagent arrangement part, an air vent 16 for the first reagent arrangement part, a connection passage 14 for connecting the reagent arrangement parts, a second reagent arrangement part 15, an air vent passage 19 for the second reagent arrangement part, and an air vent 20 for the second reagent arrangement part. One sample supply part 11 integrally serves as sample supply parts of the assay instruments, and one air vent 20 integrally serves as the air vents for the second reagent arrangement parts. In at least one assay instrument of the assay instrument assembly 2, a bilirubin oxidase-containing thy reagent 17, a magnetic particle 18, and a surfactant-containing dry reagent 22 are arranged. The materials, manufacturing method, and using method of the assay instrument assembly of the present invention are similar to those of the above-described assay instrument shown in FIGS. 1A and 1B.

In still another aspect, the present invention is a test piece to be used for bilirubin assay, including a sample-holding layer, a bilirubin oxidase-containing layer, and a surfactant-containing layer, which are laminated in the stated order. Materials composing the layers are not limited particularly, and conventionally known materials can be used such as filtering paper, glass fiber filtering paper, knitted fabrics, woven fabrics, non-woven fabrics, membrane filters, porous resin sheets, plastic films, and the like. The sample-holding layer may includes, for example, a blood cell separation film (layer) and the like. The test piece of the present invention preferably can be used in the method for assaying bilirubin according to the present invention.

In the test piece of the present invention, the sample-holding layer may be omitted. In another aspect, therefore, a test piece of the present invention includes a bilirubin oxidase-containing dry reagent layer and a surfactant-containing dry reagent layer, and the bilirubin oxidase-containing dry reagent layer and the surfactant-containing dry reagent layer are laminated in the stated order on a sample supply face. On the sample supply face, for example, a blood cell separation film (layer) may be provided. The test piece of the present invention preferably can be used in the method for assaying bilirubin according to the present invention.

The present invention is described further with reference to Examples below, though not being limited to the same.

EXAMPLE 1

Confirmation that Reaction Velocity Varies with the Order in which Reagents are Mixed It was confirmed that in the bilirubin assay in which a bilirubin oxidase (dry reagent) and a surfactant (dry reagent) were used, the order in which the reagents were mixed with an assay sample affected the reaction rate of the bilirubin oxidase.

<Preparation of Dry Reagents>

Dry reagents R1 and R2 were prepared in wells of a microplate. The respective final concentrations of the compositions in the case where the dry reagents R1 and R2 were dissolved in the assay sample were as shown in Table 1 below.

TABLE 1

| R1 | |
|---|---|
| 100 mMBES | pH 7.0 |
| 5 mM | EDTA |
| 100 U/ml | BOD |
| R2 | |
| 100 mMBES | pH 7.0 |
| 0.5% | SDS |

The dry reagent R1 was prepared as follows. First, 2.1325 g of BES (N,N-bis(2-hydroxyethy)-2-aminoethanesulfonic acid, produced by DOJINDO LABORATORIES), and 0.0931 g of EDTA-2Na-2H$_2$O were dissolved in distilled water, with the pH thereof being adjusted to 7 with use of NaOH, so as to be 50 ml in total amount (the solution thus prepared is hereinafter referred to as BOD buffer solution). 0.8163 g of a bilirubin oxidase (BOD, produced by Amano Enzyme Inc.) was dissolved with the foregoing BOD buffer solution, so as to be 20 ml in total amount. 70 μm of this bilirubin oxidase solution was placed in each well of the microplate, frozen at −80° C., and thereafter treated by freeze-drying, whereby the dry reagent R1 was obtained.

The dry reagent R2 was prepared as follows. First, 0.25 g of sodium dodecyl sulfate (SDS) was dissolved in the above-described BOD buffer solution, with pH thereof being adjusted to 7 with use of HCl, so as to be 50 ml in total amount. 50 of this SDS solution was placed in each well of the microplate, frozen at −80° C., and thereafter treated by freeze-drying, whereby the dry reagent R2 was obtained.

<Preparation of Assay Sample>

50 mg of indirect bilirubin (trade name: Bilirubin, produced by Wako Pure Chemical Industries, Ltd.) was dissolved in 2.5 ml of DMSO, and 5 ml of 0.1 M $N_2CO_3$ was added thereto. 7.5 ml of this indirect bilirubin solution was added to 150 ml of normal blood serum, and further, 3 ml of 0.1 N HCl was added thereto, whereby an indirect bilirubin sample was prepared. The concentration of this sample was measured by a conventional known liquid-system quantification method, and was found to be 27.3 mg/dl.

<Assay R1→R2

70 μl of the assay sample was placed in a well in which the dry reagent R1 was prepared, so as to dissolve the dry reagent R1, and immediately 50 μl out of 70 μl in which the dry reagent R1 was dissolved was put in a well in which the thy reagent R2 was prepared, so as to dissolve the dry reagent R2. A change in absorbance after reaction was measured by a microplate reader at a main wavelength of 450 nm and a sub-wavelength of 630 nm (hereinafter this assay in which the dry reagents R1 and R2 are used in this order is referred to as "Assay R1→R2"). The measurement was started 120 seconds after the addition of the assay sample to the dry reagent R1. Assay R2→R1 was performed in the same manner except that the dry reagents R1 and R2 were replaced with each other.

<Result>

Figure 3:
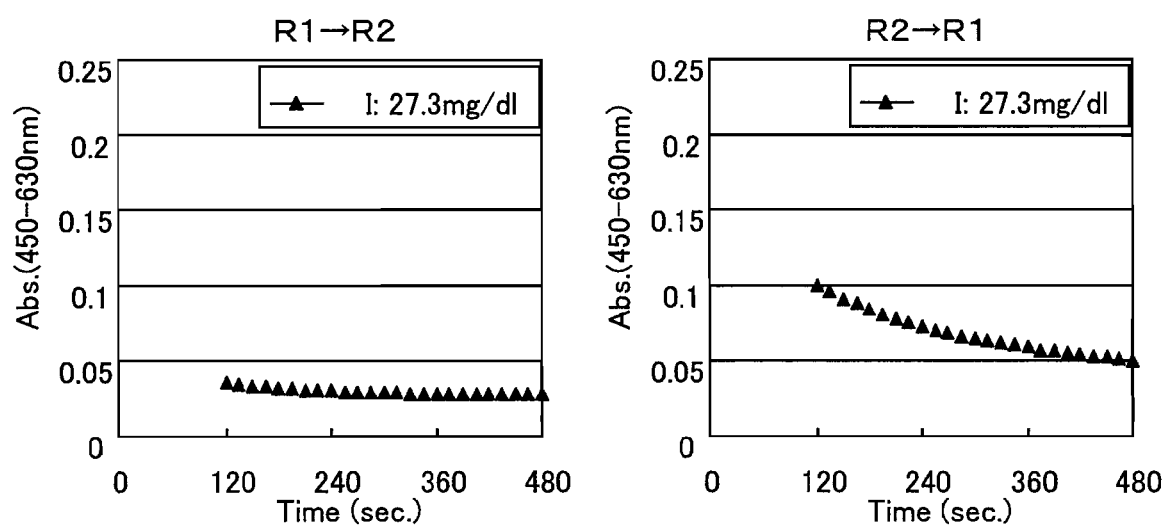
FIG. 3 show graphs of exemplary bilirubin assay results.

Exemplary results of Assay R1→R2 and Assay R2→R1 are shown in graphs in FIG. 3. As shown in FIG. 3, in the case of Assay R1→R2, namely, in the case where a bilirubin oxidase was allowed to react with a sample and thereafter a surfactant was allowed to react therewith, an absorbance substantially reached a plateau two minutes after the start as shown in the graph, from which it can be concluded that the reaction between bilirubin and the bilirubin oxidase quickly completed (the left graph of FIG. 3). On the other hand, in the case of Assay R2→R1, namely, in the case where a surfactant was allowed to react with a sample and thereafter a bilirubin oxidase was allowed to react therewith, an absorbance did not reach a plateau yet even eight minutes after the start as shown in the graph, from which it can be concluded that the reaction between bilirubin and the bilirubin oxidase did not complete (the right graph of FIG. 3). Therefore, it was confirmed that in the bilirubin assay in which a bilirubin oxidase (dry reagent) and a surfactant (dry reagent) were used, the assay time could be shortened in the case where the bilirubin oxidase was mixed with an assay sample first, as compared with the case where the surfactant was mixed therewith first.

EXAMPLE 2

Confirmation that Reaction Velocity Varies with the Order in which Reagents are Mixed In addition to the assay sample used in Example 1 (indirect bilirubin sample: 27.3 mg/di), direct bilirubin samples having concentrations of 6.0 mg/dl, 12.1 mg/dl, and 24.4 mg/dl, respectively, indirect bilirubin samples having concentrations of 8.1 mg/dl and 16.1 mg/dl, respectively, and a bilirubin sample having a concentration of 0.0 mg/dl were prepared, and were subjected to Assay R1→R2 and Assay R2→R1 in the same manners as those in Example 1. The direct bilirubin samples were prepared in the same manner as that of the indirect bilirubin sample of Example 1 except that direct bilirubin (trade name: ditaurobilirubin, produced by Promega Corporation) was used as bilirubin. The respective concentrations of the samples were adjusted by dilution with use of normal blood serum.

Figure 4:
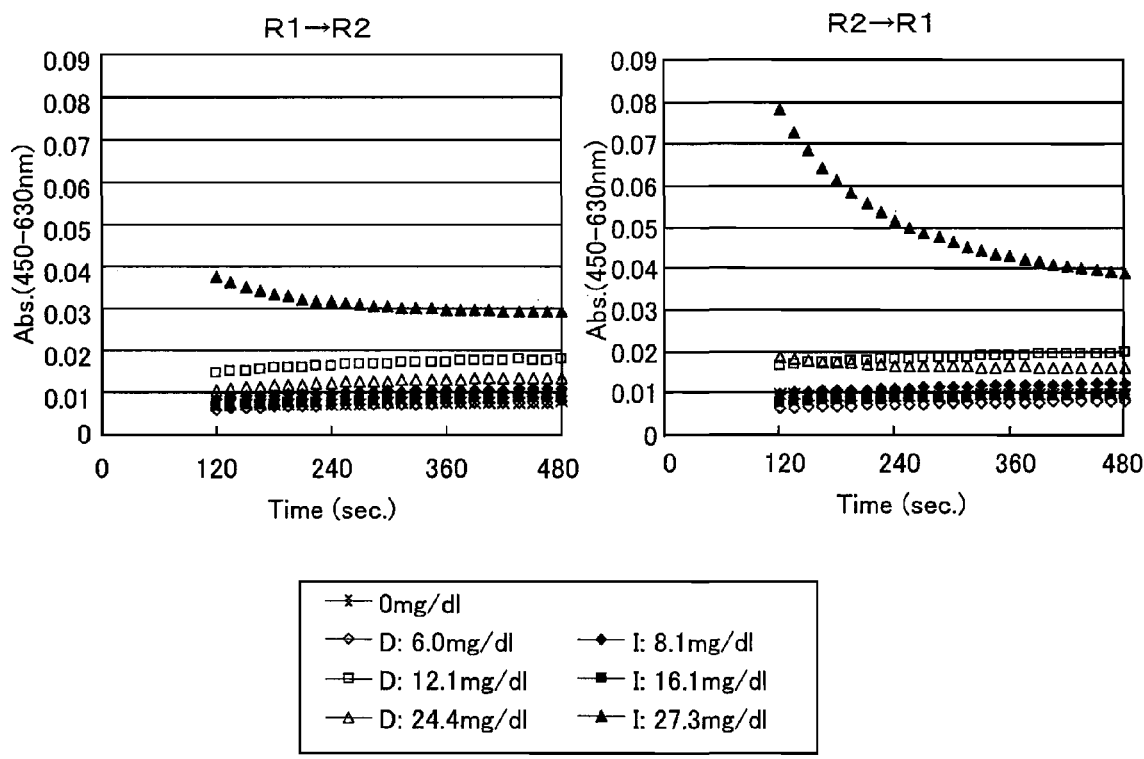
FIG. 4 show graphs of other exemplary bilirubin assay results.

Exemplary results of the assays are shown in FIG. 4. In the legends in the drawing, "D" represents direct bilirubin, and "T" represents indirect bilirubin. As shown in FIG. 4, it was confirmed that the effect of accelerating the bilirubin oxidase reaction when the reagents R1 and R2 were mixed in the order of R1→R2 was remarkable when the concentration of indirect bilirubin in the assay sample was high.

EXAMPLE 3

Confirmation that Sodium Cholate can be Used

Dry reagents R1 and R2 were prepared in the same manner as that of Example 1 except that the final concentrations of BOD in the dry reagent R1 were adjusted to 10 U/ml and 3 U/ml and that sodium cholate was used as the surfactant in the dry reagent R2 (final concentrations: 0.5 wt % and 1.5 wt %). Direct bilirubin samples and indirect bilirubin samples of various concentrations were used, and the foregoing dry reagents R1 and R2 were mixed therewith in the order of R1→R2. Then, bilirubin was assayed.

Figure 5:
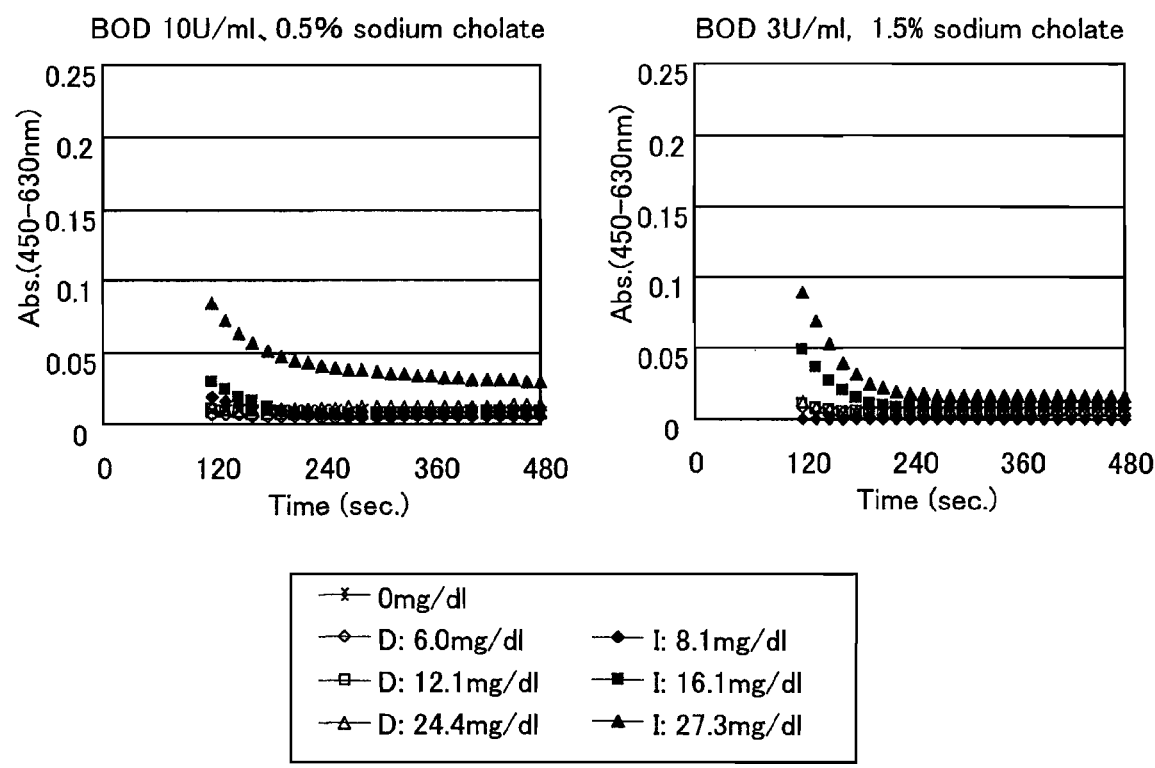
FIG. 5 show graphs of still other exemplary bilirubin assay results.

Exemplary results of the assays are shown in FIG. 5. As shown in FIG. 5, bilirubin could be assayed even in the case where sodium cholate was used. Besides, it was suggested that by increasing the concentration of the surfactant, the amount of used enzyme, i.e., the bilirubin oxidase, could be reduced.

EXAMPLE 4

Combination of Surfactants

Dry reagents R1 and R2 were prepared in the same manner as that of Example 1 except that the final concentration of BOD in the dry reagent R1 was adjusted to 1 U/ml and that a combination of SDS and sodium cholate was used as the surfactant in the dry reagent R2 (final concentrations: 0.5 wt % and 1.0 wt %). Direct bilirubin samples and indirect bilirubin samples of various concentrations were used, and the foregoing dry reagents R1 and R2 were mixed therewith in the order of R1→R2. Then, bilirubin was assayed.

Figure 6:
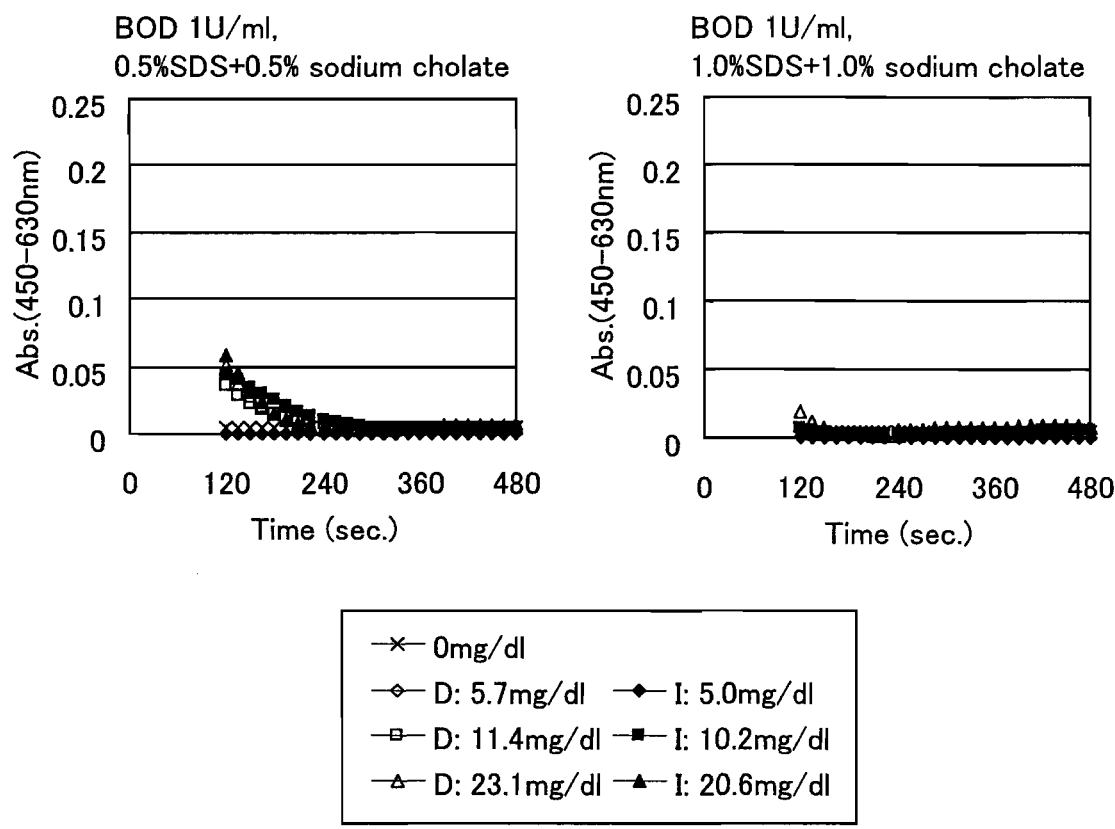
FIG. 6 show graphs of still other exemplary bilirubin assay results.

Exemplary results of the assays are shown in FIG. 6. As shown in FIG. 6, by combining surfactants, a total amount to be arranged was increased, whereby quick assay was enabled even in the case where the concentration of BOD was 1 U/ml.

INDUSTRIAL APPLICABILITY

As described above, the present invention is useful in the dry-system bilirubin assay, and is useful in, for example, medical fields such as medical examination and diagnosis.

The invention claimed is:

1. A method for assaying bilirubin in a biological sample, the method comprising:
   mixing the biological sample, a bilirubin oxidase-containing dry reagent, and a surfactant-containing dry reagent; and
   optically measuring a change caused by the mixing,
   wherein the mixing of the biological sample and the bilirubin oxidase-containing dry reagent is carried out before the mixing with the surfactant-containing dry reagent, and
   wherein the surfactant is an anionic surfactant.

2. The method according to claim 1, wherein the anionic surfactant is one or more surfactants selected from the group consisting of sodium dodecyl sulfate (SDS), sodium dodecyl benzene sulfate (SDBS), sodium polyoxyethylene lauryl ether sulfate, sodium deoxycholate, and sodium cholate.

3. The method according to claim 1, wherein the anionic surfactant is selected from the group consisting of sodium dodecyl sulfate (SDS), sodium cholate and mixtures thereof.

4. The method according to claim 1, wherein the anionic surfactant is sodium dodecyl sulfate (SDS).

5. The method according to claim 1, wherein the anionic surfactant is sodium cholate.

6. The method according to claim 1, wherein the bilirubin oxidase is derived from the group consisting of the genus *Myrothecium* and the genus *Trachyderma*.

7. The method according to claim 1, wherein the biological sample is in a liquid form.

8. The method according to claim 1, wherein the biological sample is selected from the group consisting of whole blood, blood serum, blood plasma and urine.

9. The method according to claim 1, wherein the bilirubin oxidase-containing dry reagent is prepared by drying a reagent solution comprising the bilirubin oxidase and one or more selected from the group consisting of a buffer, a stabilizer and a chelating agent.

10. The method according to claim 9, wherein the buffer is selected from the group consisting of TES (N-tris(hydroxymethyl)methyl-2-aminoethanesulfonic acid), BES (N,N-bis(2-hydroxyethyl)-2-aminoethanesulfonic acid), MOPSO (2-hydroxy-3-morpholinopropanesulfonic acid), MOPS (3-(N-morpholino)propanesulfonic acid), PIPES (piperazine-N,N'-bis(2-ethane sulfonic acid)), ADA (N-(2-acetamide)iminodiacetic acid), ACES (N-(2-acetamide)-2-aminoethanesulfonic acid) and MES (2-morpholinoethanesulfonic acid).

11. The method according to claim 1, wherein the method further comprises optically measuring a change in absorbance of the biological sample at 450 nm before the mixing of the biological sample and the bilirubin oxidase-containing dry reagent and after the mixing with the surfactant-containing dry reagent.

* * * * *